United States Patent
Sherratt et al.

(10) Patent No.: US 6,479,068 B1
(45) Date of Patent: Nov. 12, 2002

(54) THERAPEUTIC NUTRIENT REGIMEN FOR ALLEVIATING MUCOSITIS, STOMATITIS AND CACHEXIA IN ONCOLOGY PATIENTS

(75) Inventors: J. Dale Sherratt, Sherborn; Joann Somerville, Reading, both of MA (US)

(73) Assignee: Baxter International Inc., Deerfield, IL (US)

(*) Notice: Subject to any disclaimer, the term of this patent is extended or adjusted under 35 U.S.C. 154(b) by 0 days.

(21) Appl. No.: 09/609,238

(22) Filed: Jun. 30, 2000

(51) Int. Cl.[7] .............................................. A61K 47/00
(52) U.S. Cl. ...................................................... 424/439
(58) Field of Search ................................. 424/702, 439

(56) References Cited

U.S. PATENT DOCUMENTS

| | | | |
|---|---|---|---|
| 5,039,704 A | | 8/1991 | Smith et al. |
| 5,438,075 A | | 8/1995 | Skubitz et al. |
| 5,545,668 A | * | 8/1996 | Skubitz et al. ............... 514/561 |
| 6,197,295 B1 | * | 3/2001 | Hsia et al. .................. 424/93.5 |

FOREIGN PATENT DOCUMENTS

EP            204987       * 12/1986

OTHER PUBLICATIONS

Herbert G. Windmueller "Glutamine Utilization of the Small Intestine" Advances in Enzymology and Related Areas of Molecular Biology, vol. 53, pp. 201–237 (1982) Published by John Wiley & Sons.

Peter M. Anderson, M.D., Ph.D. et al. "Oral Glutamine Reduces the Duration and Severity of Stomatis after Cytotoxic Cancer Chemotherapy" Cancer, vol. 83, No. 7, pp. 1433–1439 (1998) Published by John Wiley & Sons, Inc.

Morgan Berthrong, M.D. "Pathologic Changes Secondary to Radiation" World Journal of Surgery vol. 10, No. 2, pp. 155–170 (1986) Published by Springer International.

John C. Alverdy, M.D., F.A.C.S. "Effects of Glutamine–Supplemented Diets on Immunology of the Gut" Journal of Parenteral and Enternal Nutrition, vol. 14, No. 4 Supplement, pp. 109S–113S (1990) Published by Williams & Wilkins.

Connie Ford, RN, et al. " Glutamine–Supplemented Tube Feedings Versus Total Parenteral Nutrition in Children Receiving Intensive Chemotherapy" Journal of Pediatric Oncology Nursing, vol. 14, No. 2, pp. 68–72 (1997) Published by W.B. Saunders Company.

Andrew D. Fox, M.D. et al. "Effect of a Glutamine–Supplemented Enteral Diet on Methotrexate–Induced Enterocolitis" Journal of Parenteral and Enteral Nutrition, vol. 12, No. 4, pp. 325–331 (1988) Published by ASPEN.

P. Fürst, et al. "Evidence for a nutritional need for glutamine in catabolic patients" Kidney International, vol. 36, Supplement No. 27, pp. S–287–S292 (1989) Published by Springer International.

Eng–Yen Huang, M.D., et al. "Oral Glutamine To Alleviate Radiation–Induced Oral Mucositis: A Pilot Randomized Trial" International Journal of Radiation Oncology Biology Physics, vol. 46, No. 3, pp. 535–539 (2000) Published by Elsevier.

V. Suzanne Klimberg, M.D., et al. "Glutamine, Cancer, and Its Therapy" The American Journal of Surgery, vol. 172, pp. 418–424 (1996) Published by Excerpta Medica, Inc.

V. Suzanne Klimberg, M.D., et al. "Glutamine Suppresses PGE2 Synthesis and Breast Cancer Growth" Journal of Surgical Research, vol. 63, No. 1, pp. 293–297 (Jun. 1996) Published by Academic Press.

E. Roth, et al. "Metabolic Disorders in Severe Abdominal Sepsis: Glutamine Deficiency in Skeletal Muscle" Clinical Nutrition, vol. 1, No. 1, pp. 25–41 (Mar. 1982) Published by Churchill Livingstone.

Diane Savarese et al. "Glutamine Treatment of Paclitaxel–Induced Myalgias and Arthragias" Journal of Clinical Oncology, vol. 16, No. 12, pp. 3918–3919 (Dec. 1998) Published by W.B. Saunders Company.

Keith M. Skubitz and Peter M. Anderson, "Oral glutamine to prevent chemotherapy induced stomatitis: A pilot study", *The Journal of Laboratory and Clinical Medicine*, 127(2):223–228 (Feb. 1996).

* cited by examiner

*Primary Examiner*—Alton Pryor
(74) *Attorney, Agent, or Firm*—Jeffrey C. Nichols; Mark J. Buonaiuto; Francis C. Kowalik

(57) ABSTRACT

The present invention relates to a daily regimen for oncology patient suffering from mucositis, stomatis, and cachexia wherein the daily regimen involves administering to the patient at least one dose of an oral composition in unit dosage form which comprises L-glutamine, vitamin A, vitamin C, vitamin E, and selenium; and at least four glutamine lozenges throughout the day which comprises about 2 grams of glutamine each, beginning 4–7 days prior to said treatment and continuing through said treatment.

30 Claims, No Drawings

THERAPEUTIC NUTRIENT REGIMEN FOR ALLEVIATING MUCOSITIS, STOMATITIS AND CACHEXIA IN ONCOLOGY PATIENTS

BACKGROUND OF THE INVENTION

1. Field of the Invention

The present invention relates to the use of the amino acid glutamine in combination with additional nutrients in a composition for alleviating side effects of oncology treatment in a cancer patient comprising administering to the patient a daily regimen which comprises administering (a) at least one dose of an oral composition in unit dosage form which comprises L-glutamine, vitamin A, vitamin C, vitamin E, and selenium twice daily; and (b) at least four glutamine lozenges throughout the day which comprise about 2 grams of glutamine each, beginning 4–7 days prior to said treatment and continuing through said treatment. The daily regimen allows for physical contact of mucosal membranes with glutamine as well as systemic administration for alleviating the side effects of oncology therapy.

2. Description of the Prior Art

Skubitz et al. in U.S. Pat. Nos. 5,438,075 and 5,545,668 disclose an oral glutamine composition which is used to treat oropharyngeal mucositis in patients undergoing chemotherapy or radiotherapy. The patents disclose a method of alleviating stomatitis or esophagitis originating from treatment with chemotherapy and/or radiotherapy by administering the glutamine composition described in the patent.

Anderson et al. disclose a patient study involving administration of a glutamine suspension to swish and swallow on days of chemotherapy administration and for at least 14 additional days. Anderson et al. conclude that low dose oral glutamine supplementation during and after chemotherapy significantly reduced both the duration and severity of chemotherapy-associated stomatitis and decreased the chance of patients developing mouth sores as a consequence of intensive cancer chemotherapy. See Anderson et al., Cancer, vol. 83 pages 1433–9 (1998).

Ford et al. disclose the use of total parenteral nutrition (TPN) supplemented by nasogastric glutamine-supplemented tube feedings in pediatric cancer patients receiving intensive chemotherapy alone or in combination with bone marrow transplantation. During a study of patients, Ford et al. anticipated that early glutamine supplemented tube feedings in children receiving intensive chemotherapy alone or in combination with bone marrow transplantation would result in improved nutrition with fewer infections and lower cost than TPN-supplemented patients. In addition, a shorter hospital stay and improved quality of life are anticipated. See Ford et al., J Pediatr. Oncol. Nurs., vol. 14, pages 68–72 (1997).

Huang et al., in Int. J. Radiat. Oncol. Biol. Phys., vol. 46, pages 535–9 (2000), evaluate the influence of oral glutamine on radiation-induced oral mucositis in the radiotherapy of head and neck cancer. Pursuant to the study, they conclude that oral glutamine may significantly reduce the duration and severity of objective oral mucositis during radiotherapy.

3. Discussion of the Background of the Invention

Gut toxicity is often exhibited following bolus administration of anti-neoplastic agents, but is more common when these agents are administered via continuous infusion. Continuous infusion is becoming the preferred method of administration of oncology treatment agents because continuous infusion chemotherapy results in exposure of the tumor to cytotoxic drugs for a period of time longer than other methods of administration. Thus, continuous infusion is considered to be more efficacious than bolus chemotherapy for tumors with low growth fractions. However, it is clear that continuous infusion chemotherapy exhibits a toxicity profile different from bolus drug administration, and for some drugs this may be associated with increased mucositis. Mucositis is inflammation of mucous membranes including any region in an alimentary canal. For example, the continuous infusion of doxorubicin is associated with less cardiotoxicity than bolus administration, but often mucositis as a side effect limits the amount of drug administered. Similarly, for example, the bolus administration of 5-fluorouracil is associated with leukopenia, whereas gut toxicity, including stomatitis and esophagitis, is often exhibited when the drug is administered by continuous infusion over more prolonged periods or when combined with folinic acid. Stomatitis is inflammation of the oral mucosa.

The mechanism of chemotherapy-induced mucositis appears to arise from a combination of many factors. Presumably, chemotherapy damages the rapidly dividing immature intestinal crypt cells and more superficial immature mucosal cells in the oropharynx. In addition to this direct damage, it is theorized that, as the mature epithelial cells are sloughed, damaged immature cells are exposed to pancreatic and biliary secretions resulting in further intestinal damage. This damage contributes to mucositis.

The gut is among the largest repositories of lymphoid tissue in the body and the gut-associated lymphoid tissue has been termed GALT (See Enteral Nutr., vol. 14, pages 109S–113S, (1990)). The effects of chemotherapy on this lymphoid tissue may result in an additional disruption to the gut mucosal integrity, in addition to the direct effects of chemotherapy on the enterocytes. Other factors may also be involved; in normal individuals there is a constant and closely regulated flow of energy, mediated by various metabolites, among different tissues in the body (See Adv. Enzymology, vol. 53, pages 202–231, (1982)). Chemotherapy appears to directly, or indirectly, via decreasing nutrient intake, alter the production of glutamine which is necessary for the gut. This effect has been exhibited during catabolic illness when plasma glutamine concentration often falls. It is thought that a result of mucositis is the bacterial translocation across a malfunctioning gut epithelium which is believed to play a role in the gut-related toxicity of chemotherapy and radiotherapy and thus mucositis is exhibited.

In healthy, non-stressed individuals, glutamine is a neutral, non-essential amino acid. It is the most abundant amino acid, comprising 60% of the total free amino acid pool. Because glutamine contains two nitrogen moieties it may also be one of the most versatile amino acids. Much of the nitrogen transported from the skeletal tissues to the visceral tissues is done by glutamine. As a primary fuel for rapidly dividing cells including enterocytes, colonocytes, lymphocytes and fibroblasts, it is as efficient as glucose. Oxidized glutamine provides substrate for the synthesis of purines and pyrimidines needed for DNA, RNA, and mRNA and in the kidney glutamine is involved in acid-base balance through ammonia production.

During periods of increased metabolic stress, glutamine is freely released from skeletal muscle and intracellular glutamine concentrations fall by more than 50%. Roth et al. found that in patients with abdominal sepsis survival Was related to levels of free intracellular glutamine in the blood. See Roth et al., Clin. Nutr., Vol. 1, pages 25–41 (1981). Although the body can synthesize glutamine, it is now considered a conditionally essential amino acid during periods of catabolism. Physiological glutamine synthesis rates cannot keep up with the higher requirements for the amino acid during stress. Furst et al. have suggested that during periods of stress, 15–35 grams of supplemental glutamine may be needed to preserve muscle glutamine, maintain gut integrity, provide fuel for cells with rapid turnover and improve overall nitrogen balance. See Furst et al., Kidney Int., vol. 36, pages 5287–5292 (1982).

During the past 10 years, the role of glutamine as an immunomodulator has been emerging. Tumor growth is inversely related to host glutamine reserves. In this way, tumors act as glutamine traps. Cancer cachexia is marked by massive host skeletal glutamine depletion. In vitro evidence of the dependence of tumor growth on glutamine has deterred its use in the clinical setting. However, growing in vivo evidence suggests that supplemental glutamine actually decreases tumor growth by upregulating the immune system. Glutamine is a major fuel source for immune cells, especially lymphocytes and macrophages, both key types of immune cells. In addition, glutamine has been shown to be involved with bacterial killing by neutrophils.

Lymphocytes are one class of rapidly dividing cells that utilize glutamine as a primary fuel source. Glutamine is an essential component of lymphocyte cell division in vitro. Other amino acids or combinations of glutamate plus ammonia cannot substitute for glutamine. Natural Killer (NK) cells are cytotoxic lymphocytes capable of killing tumor cells as well as producing other cytokines. Tumors do not grow well in hosts with high NK cell activity. Optimal functioning of lymphocytes, including NK cells, is dependent on adequate supplies of glutamine and glutathione. Research has indicated increases in NK cell activity when supplemental glutamine is administered. See Klimberg et al., J. Surg. Res., vol. 63, pages 293–297 (1996).

Radiation enteritis remains a significant clinical problem for patients receiving ionizing radiation to the abdominal and pelvic areas. The mucosal injuries seen with radiation to these areas include destruction of crypt cells, decreased villous height, ulceration and necrosis of the gastrointestinal epithelium. See Berthrong et al., World J. Surg., vol. 10, pages 155–170 (1986). The mucosal injuries are manifested by abdominal pain, bloody diarrhea, malabsorption and in some cases bacterial translocation. Severe cases can be complicated by strictures, obstructions, perforations, and fistula formation.

The role of glutamine as a preferred fuel for the gastrointestinal tract is well known. See, for example, U.S. Pat. No. 5,039,704 to Smith et al. Research has delineated the role of glutamine as both protector before and healer after radiation therapy. It appears that glutamine exerts a positive effect through three distinct routes; as a primary cellular fuel for enterocytes, as a precursor for nucleotides needed for cell regeneration and as a source of glutathione, a potent antioxidant.

Oral glutamine taken prior to radiation appears to exert a protective effect by bolstering gut glutamine metabolism which is evidenced by an increase in the number and height of intestinal cells as well as an overall increased proliferation of cells. Taken during or after radiation, oral glutamine lessens the degree of damage and accelerates healing of the irradiated bowel by improving cell structure and upregulating gut glutamine metabolism. See Klimberg et al., Am. J. Surg., vol. 172, pages 418–424 (1996). However, oral glutamine alone is usually insufficient since patients experience difficulty in swallowing and retaining the administered glutamine.

As previously mentioned, cytotoxic oncology treatment often produces gastrointestinal injury resulting in mucositis, stomatitis and enterocolitis. The severity of these effects may preclude dose escalation and, in fact, may warrant dose reductions. Several beneficial effects of supplemental glutamine in chemotherapy induced enterocolitis have been recognized. These include improved nutritional status, decreased intestinal injury, decreased bacterial translocation, reduced endotoxemia and improved survival. See, e.g., Fox et al., JPEN, vol. 12, pages 325–331 (1988) Further studies have shown that supplemental oral glutamine can enhance the effect of methotrexate, an anti-neoplastic agent, while decreasing morbidity to the host.

Because of the high incidence of chemotherapy induced morbidity there has been great interest in finding agents that may increase tolerance to antineoplastic treatments. Skubitz et al., in J. Lab. Clin. Med., vol. 127, pages 223–228 (1996) describe a study on the effects of supplemental glutamine on chemotherapy induced mucositis. Chemotherapy agents used by Skubitz et al. include doxorubicin, etoposide, ifosfomide, and carboplatinum. Patients received twice daily glutamine supplemented swish and swallow solutions on days 1 through 28 of chemotherapy. Skubitz et al. found significant reductions in the level of mucositis as well as the duration of mucositis. Subjectively, the patients felt that the mucositis was less severe which is important as a quality of life issue.

One of the major effects of glutamine supplementation is its protective effect on the gut barrier. Glutamine is the major fuel for the gut enterocyte and glutamine deficiency will decrease the gut mucosal barrier function leading to 'gut leak'. By protecting the gut barrier, patients undergoing chemotherapy and/or radiation are able to better respond to treatment because of increased energy and decreased levels of mucositis, stomatitis and cachexia.

Glutamine has been studied with regards to limiting non-gastrointestinal chemotherapy related toxicity and it has been found to increase the survival rate in cancer patients receiving cyclophosphamide. The glutamine supplementation maintained normal cardiac glutathione levels decreasing cardiotoxicity. See, e.g., Klimberg et al., Academic Surgery Conference (1993). It also has been reported that the use of oral glutamine may prevent paclitaxel-induced myalgias and arthralgias. See Savarese et al., J. Clin. Oncology, vol. 12, pages 3918–3919 (1998).

Traditional diets taken by mouth usually contain less than 10 grams of glutamine per day. During periods of severe metabolic stress or catabolic insult 20 to 40 grams of glutamine may be required to maintain homeostasis. Recent studies have shown glutamine to be more effective when administered via the enteral route. Ready to use enteral supplements are not supplemented with glutamine because of stability issues. Standard pills or capsules are expensive and contain very small amounts of glutamine (500 –1000 mg) relative to the daily dosages shown to be effective (30 grams). A powdered glutamine supplement is most desirous because it is cost effective, easy to use, well absorbed, well tolerated, and safe. Thus, a daily regimen to administer a powdered glutamine nutritional supplement painlessly and effectively is needed.

Furthermore, the incidence of malnutrition in patients undergoing anti-neoplastic treatments is well known. Cancer cachexia is exhibited by profound weight loss and is secondary only to macronutrient (protein, fat, and carbohydrate) deficiency, negative energy balance, and inefficient metabolism. Cachexia is the gradual bodily deterioration of muscle mass and weight loss. Cancer cachexia is the weight loss and deterioration of muscle mass associated with a flourishing tumor. It has been suggested that micronutrient (vitamin, mineral, and trace elements) deficiency is prevalent in cancer patients and that antioxidants may be particularly importance since radiation and chemotherapy, which damage both healthy and malignant cells, are oxidative processes. Because cancer cells do not absorb antioxidants as efficiently as healthy cells, it may be possible to support normal tissues with antioxidants while making the oxidative process more selectively toxic to malignant cells. Under conditions of antioxidant depletion, fewer oxidants are needed for injury to occur. The provision of antioxidant nutrients and precursors such as vitamins A, C and E, and selenium may offer protection to healthy cells against oxidative injury by antineoplastic therapy.

Therefore, a daily regimen including micronutrient and antioxidants as well as glutamine supplementation for alleviating cachexia, mucositis and stomatis in cancer patients is needed.

SUMMARY OF THE INVENTION

The present invention provides a method of alleviating mucositis, stomatitis, and cachexia in cancer patients by administering a daily regimen, to the patients 4–7 days prior to oncology therapy, of at least one oral unit dosage form of glutamine with micronutrients and antioxidants two times a day (e.g, vitamin A, vitamin C, vitamin E, and selenium) and at least four doses of glutamine in the form of a lozenge administered throughout the day.

In a preferred embodiment, the unit dosage form comprises about 7–12 g of L-glutamine, about 4,000–7,000 IU of vitamin A, about 100–300 mg of vitamin C, abut 50–150 IU of vitamin E and about 25–100 μg of selenium.

In a particularly preferred embodiment, the unit dosage form comprises about 10 g of L-glutamine, about 6,500 IU of vitamin A, about 200 mg of vitamin C, about 100 IU of vitamin E, and about 50 μg of selenium.

In a preferred embodiment, at least two unit dosage forms of the glutamine composition are administered twice daily to a patient in need thereof as a component of the daily regimen.

In an especially preferred embodiment, the twice daily administration occurs once in the morning and once in the evening.

In a preferred embodiment, at least three unit dosage forms of the glutamine composition are administered twice daily to a patient in need thereof as a component of the daily regimen.

In another preferred embodiment, at least three glutamine lozenges are administered throughout the day to a patient in need thereof as a component of the daily regimen.

In a particularly preferred embodiment, at least four lozenges are administered throughout the day to a patient in need thereof as a component of the daily regimen.

In another particularly preferred embodiment, at least five lozenges are administered throughout the day to a patient in need thereof as a component of the daily regimen.

In another particularly preferred embodiment, at least six lozenges are administered throughout the day to a patient in need thereof as a component of the daily regimen.

In another embodiment of the invention, the daily regimen is initiated 4 days prior to the oncology treatment, 5 days prior to the oncology treatment, 6 days prior to the oncology treatment, or 7 days prior to the oncology treatment.

Additional objects, features and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

DETAILED DESCRIPTION OF THE PREFERRED EMBODIMENTS

The present invention relates to a method of alleviating mucositis, stomatis, and cachexia in patients undergoing oncology therapy by administering as a daily regimen, a glutamine micronutrient composition in unit dosage form which includes the amino acids glutamine, vitamins and trace inorganic minerals twice daily and administering at least four glutamine lozenges throughout the day. The daily regimen alleviates the side effects of stomatitis, mucositis, and cachexia associated with oncology therapy.

Glutamine is the most abundant amino acid in the body comprising two thirds of the amino acid pool. Under normal conditions glutamine is a non-essential amino acid and requirements can be met by endogenous production. Synthesis of glutamine occurs mainly in skeletal muscle from any of the other amino acids in muscle protein via the generation of alpha ketoglutatrate which can then be converted to glutamate and then to glutamine. However, in patients undergoing oncology therapy, glutamine is an essential amino acid and exogenous glutamine is essential. As endogenous production of glutamine is totally inadequate to meet the increased needs during injury, exogenous glutamine is needed. As previously stated a glutamine deficiency state is well recognized during chemotherapy and radiotherapy. The intra and extracellular functions of glutamine are therefore impaired.

Because of the importance of glutamine in maintaining muscle mass, bodily tissues and inflammation associated with mucosal regions, supplementation of glutamine to oncology patients is desired as beneficial toward alleviating the side effects of chemotherapy and radiation therapy and the present method provides an effective and straightforward means for providing the supplementation.

Glutamine assists by its anti-catabolic effects. Glutamine is a primary fuel for proliferating fibroblasts and macrophages both key cells in the wound healing process. Glutamine is the primary amino acid used by the fibroblasts as an energy source in order to make collagen. Macrophages direct the healing process via release of growth factors. Macrophages depend on glutamine for growth factor production. Due to the increased usage, a glutamine deficiency state can occur rapidly. A unit dosage of the composition administered in the method according to the present invention may contain between about 8 grams to 15 grams of L glutamine. In a particularly preferred embodiment, the unit dosage form contains 10 g of L-glutamine. A preferred dosage is between 10 and 30 grams of L-glutamine per day to alleviate mucositis, stomatitis and cachexia. Thus, at least one unit dosage would be administered twice daily. It is preferred that two to three unit dosages would be administered twice daily.

Vitamins are organic substances that are essential in humans for growth and homeostasis. Vitamins are essential nutrients found in very small quantities in the body. Each has a name defined by a letter as well as a chemical name. These compounds play a key role in metabolism, growth and homeostasis and therefore are especially important in maintenance of body mass and the ability to effectively nourish the body are important for survival. Vitamins, in general, are not chemically related and as a result, each has a variety of unrelated functions.

Fat-soluble vitamins (such as A, D, E, K) are absorbed in the intestinal tract with lipids and require bile salts for absorption. These vitamins can be stored, to some degree, so toxicity can occur with excessive use.

The water soluble vitamin, vitamin C, cannot be made by the body and must be consumed from outside sources. Since it has a very short half life (hours), daily consumption of additional quantities outside of the average intake from foods normally consumed is required in oncology patients to avoid a deficiency state. The role of vitamin C (ascorbic acid) in the body is very complex, despite its simple structure. It is water soluble, so distribution is in the total body water space. A number of important functions for vitamin C are recognized. The most prominent role is as an antioxidant. Vitamin C is present in plasma and cell cytosol as an antioxidant. Vitamin C is important in maintaining vitamin E and glutathione (GSH) in its reduced form after oxidation by oxidants. Ascorbic acid also plays a critical role in fatty and metabolism through carnitine production as well as its role in maintaining neutrophil functions.

Plasma and cell levels of vitamin C have been reported in oncology patients. A unit dosage of the composition administered in the inventive method may contain between about 100 mg to about 300 mg of vitamin C. In a particularly preferred embodiment, the unit dosage form contains about 200 mg of vitamin C. A preferred dosage is between about 200 mg and about 600 mg of vitamin C per day to replete this state of catabolic deficiency. Thus, at least one unit dosage wold be administered twice daily. It is preferred that two to three unit dosages would be administered twice daily.

The carotenoids are a fat soluble formula of 40 carbon esters which include carotene, a potent antioxidant as well as vitamin A precursor. A portion of exogenous β-carotene will be converted to Vitamin A. In the method of the invention, vitamin A in the unit dosage form is provided as β-carotene.

Vitamin A is a fat soluble multipurpose substance involved in immune defense responses and has potent antioxidant activity, similar to vitamin E, decreases lipid peroxidation. Vitamin A, also known as retinol, is transported on retinol binding protein (RBP). A decrease in RBP, which occurs post injury, will impair retinol delivery to tissues. As opposed to water soluble vitamins, vitamin A is stored in the liver.

A unit dosage of the composition administered in the inventive treatment method may contain between about 4,000 IU to about 7,000 IU of vitamin. In a particularly preferred embodiment, the unit dosage form contains about 6,500 IU of vitamin A. A preferred dosage is between about 6,500 IU and about 18,500 IU of vitamin A per day to replete this state of catabolic deficiency, assuming that a portion of the β-carotene administered will be converted to vitamin A. Thus, at least one unit dosage would be administered twice daily. It is preferred that two to three unit dosages would be administered twice daily.

The main antioxidant activity function of vitamin E is to avoid cell-membrane damage oxidants. Vitamin E, which resides in the fat layer of the cell membrane, acts as an antioxidant by becoming oxidized to protect the surrounding membrane lipid. In addition, vitamin E is most important in preventing the lipid peroxidation chain reaction, which can self perpetuate in the absence of vitamin E. A deficiency of vitamin E will lead to a potentiation of oxidant induced cell membrane damage. Oxidized vitamin E is returned to its antioxidant reduced form by cytosol reduced vitamin C and glutathione (GSH) which in turn becomes oxidized. GSH needs to be replaced continuously as it can be lost from the cell once in the oxidized form. Therefore, maintaining adequate cell membrane protection means levels of vitamin E, vitamin C and GSH must be maintained. Vitamin E has also been shown to enhance the immune response. Vitamin E levels decrease after chemotherapy or radiation therapy due to consumption by released oxidant and lack of adequate replacement. Plasma and tissue levels decreased in 24–48 hours after oncology treatment but replacement often lags well behind these losses.

A decrease in vitamin E levels in patients corresponds to an increase in plasma lipid peroxides which are markers of oxidant damage. Since vitamin E is fat soluble, parenteral replacement is limited. Administration by the oral route as soon as possible is the optimum approach. A unit dosage of the composition administered in the inventive method may contain between about 50 IU to about 150 IU of vitamin E. In a particularly preferred embodiment, the unit dosage form contains about 100 IU of vitamin E. A preferred dosage is about 100 IU and about 300 IU of vitamin E per day to replete this state of catabolic deficiency. Thus, at least one unit dosage would be administered twice daily. It is preferred that two to three unit dosages would be administered twice daily.

Micronutrients are essential for cellular function. Micronutrients useful in the unit dosage form of the present inventive method include selenium. They are called nutrients because of their key role in metabolism, but these compounds and elements are also involved in many other aspects of homeostasis, antioxidant protection and immune function. The term "micro" is used because of the extremely small amounts found in the circulation. However small the amount, their concentrations are critical to cellular function.

Selenium is present in all tissues in large part due to its critical role in cell glutathione antioxidant protection as a key cofactor for the enzyme glutathione peroxidase. Selenium absorption is in the range of 50 to 100% depending on the carrier. Selenium in addition to its well known role as an antioxidant cofactor plays a role in a number of enzyme systems central to metabolic activity especially in the function of the cytochrome P450 system. Also, selenium is required for thyroid function activity. A unit dosage of the composition according to the present invention may contain between about 25 $\mu$g to about 100 $\mu$g of selenium. In a particularly preferred embodiment, the unit dosage form contains about 50 $\mu$g of seleniumE. A preferred dosage is between about 50 $\mu$g and about 200 $\mu$g of selenium per day to replete this state of catabolic deficiency. Thus, at least one unit dosage would be administered twice daily. It is preferred that two to three unit dosages would be administered twice daily.

In addition to containing the above recited ingredients, the unit dosage form contains a carbohydrate source. The carbohydrate source is selected from the group consisting of maltodextrin, dextrose, sucrose, fructose and other sugars.

Further, the unit dosage form may contain a pharmaceutically acceptable carrier selected from the group consisting of a diluent, an excipient, and a tableting additive.

Still further, the unit dosage form may contain additive agents selected from the group consisting of a sweetener, a flavor, and a texture agent.

Methods of Dosing

The dosage administered to patients is guided by a physician skilled in the art on a case by case basis. Patients may receive multiple doses of the unit dosage form per day depending on the amount of the unit dosage form needed for the patients' particular condition, nutritional needs, and body size. Where the compositions contain about 10 g glutamine, on average, patients preferably will receive 2 to 3 doses per day but doses can range from 1 dose per day to a much higher level as determined by the patient's physician or health care provider.

A unit dosage form means that the oral glutamine composition which constitutes part (a) of the daily regimen in the inventive method is administered in a convenient form, such as, a premeasured lyophilized powder which can be reconstituted and administered to the patient as part of a daily regimen. This can be mixed with juice, tea or another form of liquid. The dosage can also be administered by mixing the lyophilized powder into moist food such as applesauce or puddings.

Patients may receive multiple doses of the glutamine lozenge per day depending on the amount of the composition needed for the patients' particular condition, nutritional needs, and body size. The glutamine lozenges contain about 2–2.5 grams of glutamine per lozenge and it is preferred that 4–5 lozenges are administered throughout the day.

Methods of Manufacture

The unit dosage form in the claimed method can be made by methods known to those skilled in the art. The elements comprising the unit dosage form are prepared by standard methods of blending and mixing at temperatures and moisture contents which allow blending to take place. The elements comprising the composition are preferably utilized in a dispersable form.

In another embodiment, the unit dosage form can be prepared using a standard wet process involving taking the product into a slurry, then processing it through heating it to high temperatures known to those skilled in the art then placing it into a separate chamber where it is blended and granulated.

The lozenges may be prepared by heating the lozenge base (e.g., a mixture of a sugar and glutamine) under vacuum to remove excess water and the remaining components are then blended into the mixture. The resulting mixture is then drawn into a continuous cylindrical mass from which the individual lozenges are formed. The lozenges are then cooled, subjected to a visual check and packed into suitable packaging.

In another embodiment, a slurry is formed with glutamine and a flavoring agent, the solvent is removed and the mixture is compressed into round shaped lozenges.

Methods of Administration

The methods of administration of the composition in unit dosage form can be either oral dosing or via a feeding tube. For an oral dose, at least one unit dosage form of the oral glutamine composition is admixed with a beverage or a moist semi-solid food at room temperature. It is recommended that ice cold beverages and liquids be avoided for admixture with the unit dosage of the glutamine composition. For use with a feeding tube, a unit dosage form of the glutamine composition is admixed with at least 60 cc of water and infused to a patient via a syringe to a feeding tube. The feeding tube is flushed with additional water and feeding via the tube is continued as per normal use.

Administration of the lozenge is via an oral route as the patient is administered the lozenge and the lozenge is sucked until it dissolves in the mouth thus effecting additional oral administration of glutamine.

Other embodiments of the invention will be apparent to those skilled in the art from consideration of the specification and practice of the invention disclosed herein. It is intended that the specification be considered as exemplary only, with the true scope and spirit of the invention being indicated by the following claims.

As used herein and in the following claims, singular articles such as "a", "an", and "one" are intended to refer to singular or plural.

What is claimed is:

1. A method of alleviating stomatitis, mucositis and cachexia associated with oncology treatment in a patient comprising administering to said patient in need thereof a daily regimen which comprises,
   (a) at least one dose of an oral composition in unit dosage form which consists essentially of L-glutamine, vitamin A, vitamin C, vitamin E, selenium, and optionally a carbohydrate source, administered at least two times a day; and
   (b) at least four glutamine lozenges administered throughout the day wherein about 2 to about 2.5 grams of glutamine is present in each of said lozenges.

beginning 4–7 days prior to said treatment and continuing through said treatment.

2. The method of claim 1, wherein at least three said unit dosages are administered to a patient.
3. The method of claim 1, wherein at least four said unit dosages are administered to a patient.
4. The method of claim 1, wherein at least five said lozenges are administered to a patient.
5. The method of claim 1, wherein at least six said lozenges are administered to a patient.
6. The method of claim 1, wherein at least one said unit dosage form is administered in the morning and one said unit dosage form is administered in the evening.
7. The method of claim 1, wherein about 7–12 g of L-glutamine is present in said unit dosage form.
8. The method of claim 1, wherein about 4,000–7,000 IU of vitamin A is present in said unit dosage form.
9. The method of claim 1, wherein about 100–300 mg of vitamin C is present in said unit dosage form.
10. The method of claim 1, wherein about 50–150 IU of vitamin E is present in said unit dosage form.
11. The method of claim 1, wherein about 25–100 :g of selenium is present in said unit dosage form.
12. The method of claim 1, wherein to said oncology treatment.
13. The method of claim 1, wherein said daily regimen is initiated 5 days prior to said oncology treatment.
14. The method of claim 1, wherein said daily regimen is initiated 6 days prior to said oncology treatment.
15. The method of claim 1, wherein the daily regimen is initiated 7 days prior to said oncology treatment.
16. The method of claim 1, wherein the carbohydrate source is present.
17. The method of claim 1, wherein said unit dosage form comprises about 10 g of L-glutamine, about 6,500 IU of vitamin A, about 200 mg of vitamin C, about 100 IU of vitamin E, and about 50 $\mu$pg of selenium.
18. The method of claim 1, wherein about 8–15 g of L-glutamine is present in said unit dosage form.
19. A method of alleviating stomatitis, mucositis and cachexia associated with oncology treatment in a patient comprising administering to said patient in need thereof a daily regimen which comprises, (a) at least one dose of an oral composition in unit dosage form which consists essentially of L-glutamine, vitamin A, vitamin C, vitamin E, selenium, and a carbohydrate source selected from the group consisting of maltodextrin, dextrose, sucrose and fructose, administered at least two times a day; and (b) at least four glutamine lozenges administered throughout the day wherein about 2 to about 2.5 grams of glutamine is present in each lozenge beginning 4–7 days prior to said treatment and continuing through said treatment.

20. A method of alleviating stomatitis, mucositis and cachexia associated with oncology treatment in a patient comprising administering to said patient in need thereof a daily regimen which comprises, (a) at least one dose of an oral composition in unit dosage form which consists essentially of L-glutamine, vitamin A, vitamin C, vitamin E, selenium and a pharmaceutically acceptable carrier selected from the group consisting of a diluent and an excipient, administered at least two times a day; and (b) at least four glutamine lozenges administered throughout the day wherein about 2 to about 2.5 grams of glutamine is present in each lozenge beginning 4–7 days prior to said treatment and continuing through said treatment.

21. A method of alleviating stomatitis, mucositis and cachexia associated with oncology treatment in a patient comprising administering to said patient in need thereof a daily regimen which comprises, (a) at least one dose of an oral composition in unit dosage form which consist essentially of L-glutamine, vitamin A, vitamin C, vitamin E, selenium and additive agents selected from the group consisting of a sweetener, a flavor and a texture agent, administered at least two times a day; and (b) at least four glutamine lozenges administered throughout the day wherein about 2 to about 2.5 grams of glutamine is present in each lozenge, beginning 4–7 days prior to said treatment and continuing through said treatment.

22. A method of alleviating stomatitis, mucositis and cachexia associated with oncology treatment in a patient comprising administering to said patient in need thereof a daily regimen which comprises, (a) at least one dose of an oral composition in unit dosage form which consist essentially of L-glutamine, vitamin A, vitamin C, vitamin E, and selenium administered at least two times a day, wherein said unit dosage form comprises a premeasured lyophilized water-soluble rapidly dissolving powder; and (b) at least four glutamine lozenges administered throughout the day wherein each glutamine lozenge comprises about 2 to about 2.5 grams of glutamine, beginning 4–7 days prior to said treatment and continuing through said treatment.

23. A method of alleviating stomatitis, mucositis and cachexia associated with oncology treatment in a patient comprising administering to said patient in need thereof a daily regimen which comprises, (a) at least one dose of an oral composition in unit dosage form which consist essentially of L-glutamine, vitamin A, vitamin C, vitamin E, and selenium administered at least two times a day, wherein said unit dosage form is admixed with a beverage or semi-solid food for oral administration; and at least four glutamine lozenges administered throughout the day wherein about 2 to about 2.5 grams of glutamine is present in each lozenge, beginning 4–7 days prior to said treatment and continuing through said treatment.

24. A method of alleviating stomatitis, mucositis and cachexia associated with oncology treatment in a patient comprising administering to said patient in need thereof a daily regimen which comprises, (a) at least one dose of an oral composition in unit dosage form which consist essentially of L-glutamine, vitamin A, vitamin C, vitamin E, and selenium administered at least two times a day, wherein said unit dosage form is adapted for tube-feeding; and (b) at least four glutamine lozenges administered throughout the day wherein of glutamine is present in each lozenge;

beginning 4–7 days prior to said treatment and continuing through said treatment.

25. A method of alleviating stomatitis, mucositis and cachexia associated with oncology treatment in a patient comprising administering to said patient in need thereof a daily regimen which comprises, (a) at least one dose of an oral composition in unit dosage form which consist essentially of about 10 g L-glutamine, about 6,500 IU of vitamin A, about 200 mg of vitamin C, about 100 IU of vitamin E, about 50 $\mu$g of selenium, and maltodextrin, administered at least two times a day; and (b) at least four glutamine lozenges administered throughout the day wherein about 2 to about 2.5 grams of glutamine is present in each lozenge, beginning 4–7 days prior to said treatment and continuing through said treatment.

26. A kit for alleviating stomatitis, mucositis and cachexia comprising:

(a) at least one dose of an oral composition in unit dosage form which comprises L-glutamine, vitamin A, vitamin C, vitamin E, and selenium; and (b) at least 4 glutamine lozenges which each comprise about 2 to about 2.5 grams of glutamine.

27. The kit of claim 26, wherein the kit contains at least two oral compositions of the unit dosage form.

28. A kit for alleviating stomatitis, mucositis and cachexia comprising:

(a) at least one dose of an oral composition in unit dosage form which comprises L-glutamine, vitamin A, vitamin C, vitamin E, selenium and a carbohydrate source; and (b) at least 4 glutamine lozenges which each comprise about 2 to about 2.5 grams of glutamine.

29. The kit of claim 28, wherein the carbohydrate source is selected from the group consisting of maltodextrin, dextrose, sucrose, and fructose.

30. A method of alleviating stomatitis, mucositis and cachexia associated with oncology treatment in a patient comprising administering to said patient in need thereof a daily regimen which comprises, (a) at least one dose of an oral composition in unit dosage form which consist essentially of L-glutamine, vitamin A, vitamin C, vitamin E, and selenium administered at least once a day; and (b) glutamine lozenges administered throughout the day wherein each about 2 to about 2.5 grams of glutamine is present in each lozenge, beginning 4–7 days prior to said treatment and continuing through said treatment.

* * * * *